United States Patent [19]

Offenhartz

[11] Patent Number: 5,609,569
[45] Date of Patent: Mar. 11, 1997

[54] DRESSING FOR AXILLA AND UPPER TORSO

[75] Inventor: Colin O'D. Offenhartz, Chappaqua, N.Y.

[73] Assignee: Exu-Dry Wound Care Products, Inc., Bronx, N.Y.

[21] Appl. No.: 427,197

[22] Filed: Apr. 24, 1995

[51] Int. Cl.$^6$ ............................................. A61F 5/00
[52] U.S. Cl. .................... 602/61; 602/4; 602/20; 602/62
[58] Field of Search ................ 602/20, 21, 61, 602/62, 4, 58, 47; 128/869, 874

[56] References Cited

U.S. PATENT DOCUMENTS

| | | | |
|---|---|---|---|
| 4,360,015 | 11/1982 | Mayer | 602/47 |
| 4,446,858 | 5/1984 | Verter | 602/20 X |
| 4,667,665 | 5/1987 | Blanco et al. | 604/378 |
| 4,909,243 | 3/1990 | Frank et al. | 602/58 |
| 5,019,064 | 5/1991 | Eilender | 604/378 |
| 5,095,894 | 3/1992 | Marble | 602/4 X |

FOREIGN PATENT DOCUMENTS 4306596  10/1993  Germany ........................... 602/61

OTHER PUBLICATIONS

"The complete line of FRASTEC Wound Care Products" (Apr. 1994) (pamphlet published by Frastec Wound Care Products, a company based in New York, New York).

*Primary Examiner*—Richard J. Apley
*Assistant Examiner*—Kim Lee
*Attorney, Agent, or Firm*—Lackenbach Siegel Marzullo Aronson & Greenspan, P.C.

[57] ABSTRACT

A dressing is described for covering the axilla and upper torso areas of a patient. The dressing is formed of a sheet of conformable material and includes a rear back portion which covers at least part of the patient's back. The rear back portion forms a first sleeve portion. At least one front chest portion is provided which covers at least a part of the patient's chest, the front chest portion also forming a second sleeve portion. The first and second sleeve portions together form a generally fitted body dressing which includes at least a partial length of sleeve to receive an arm of the patient. Hook and loop fastener tapes, which are preferably color coded, are used to releasably secure the first and second sleeve portions and for selectively opening the sleeve to expose the shoulder, axilla and upper torso of the patient. In this manner, the dressing can be quickly and safely placed on and removed from the patient with minimal inconvenience and trauma to the injuries sustained by the patient.

18 Claims, 4 Drawing Sheets

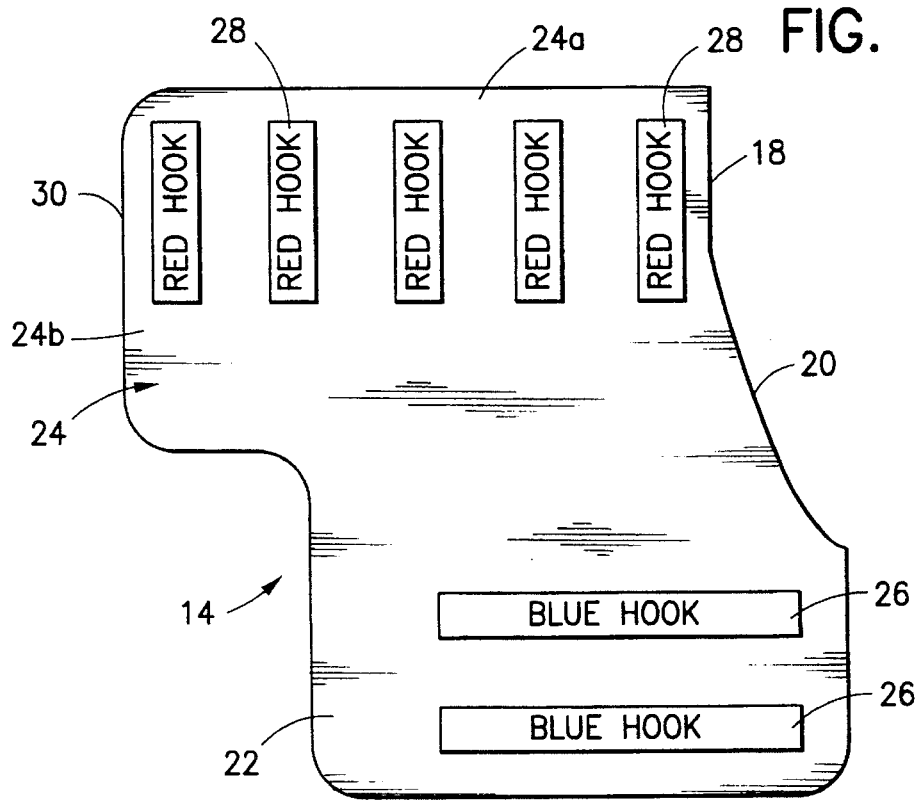
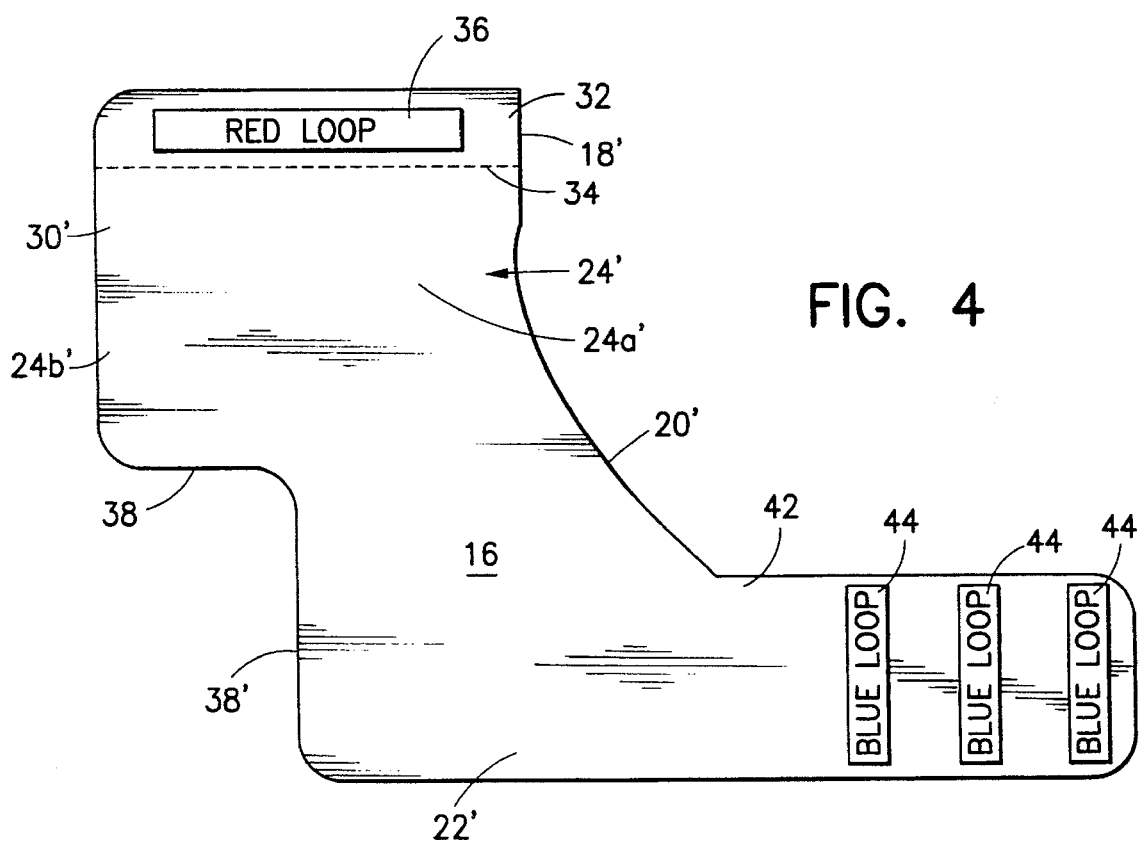

DRESSING FOR AXILLA AND UPPER TORSO

FIELD OF THE INVENTION

This invention generally relates to wound dressings, and more particularly, to a wound dressing for the axilla and the upper torso of a patient.

BACKGROUND OF THE INVENTION

Surgical and wound dressings which absorb bodily exudates and maintain fluids and topical medication at the skin surface for use in the treatment of burn patients are generally well known in the medical arts. Sterile dressings of this type maintain an incision free of lint or other contaminants which can lead to the complication of granulomas. Additionally, non-adherence to a wound or incision is necessary in order to minimize pain associated with the removal and replacement of the dressings, as well as minimize wound trauma and its associated risks of infection and delayed healing.

By way of example, the treatment of burns involves a periodic exuding of bodily liquids such as lymph and blood. In order to treat such symptoms, it is necessary to employ a bandage which is non-adherent and highly absorbent to effect dispersion of bodily discharges. Such dressings must also have the capacity to absorb fluids and medicaments in order to guard against infection and dehydration of the patient.

Another application for wound dressings is the care of surgery patients. One specific example of such surgery is radical mastectomy. This type of surgery, which can affect either or both the right and left side of a woman's chest can be particularly problematic because of the significant discharges of exudates and the need to maintain the dressing at its optimum functional capacities. It is also necessary, with dressings for the upper torso of the body, for medical personnel to be able to frequently examine the wound with minimum discomfort to the patient and, of course, with minimum damage to the sensitive wound tissue itself. Since radical mastectomy frequently also involves removal of lymphatic glands in the axilla or the region underneath the arm, that region, as well, must be properly drained and guarded. Typically, gauze, in the form rolls, stretch wraps, sponges and vests, as well as ABD pads have been used. However, these aforementioned products have similar problems. These dressings stick to the wound and cause extreme or severe discomfort to the patient during dressing changes. These dressings also destroy new tissue being formed while leading to friction and shearing of new tissue. This allows maceration of the wound. Dressing and dressing changes are also time consuming due to the need to (a) unwrap multiple layers of dressing material; and (b) re-wrap new multiple layers of dressing material.

Lack of wicking action, which does not allow absorption by an entire dressing area, leads to "strike-through". This occurs when drainage is concentrated to the area equal to the size of the wound. Drainage has nowhere else to go but "out" the back side of the dressing. When strike-through occurs the following results: there is poor utilization of dressing material area which is costly. Also, one cannot re-use the dressing material and, therefore, more frequent dressing changes, are required which cause repeated pain and discomfort to the patient and take additional nursing time. Additionally, this does not allow the patient to heal properly and the patient soils garments and beddings which leads to additional costs for cleaning and/or replacement. Because healing is retarded, additional tissue is destroyed and leads to dead tissue odors which can be embarrassing to patients and unpleasant to staff. Use of excessive layers of dressing materials to try and absorb as much exudate as possible, as suggested, is time wasteful, consumes excessive material and increases costs. If too much material is used the dressing becomes too bulky and this may, in turn, limit the patient's mobility or limit the free range of motion and make the dressing extremely uncomfortable to the patient.

Medical staff cannot evaluate wounds without at least partially removing dressings. This, as indicated, causes pain and discomfort to the patient, destroys new tissue and is time consuming. The known approaches require additional materials (i.e. tape) to secure the dressing materials in place. Using tape leads to tape burns, sensitivity due to allergies to tape substrates and adhesives. Skin tears upon removal is common. When wounds cover large areas unavailability of healthy skin to which tape can be applied leads to poor conformance to the wound which is necessary for good wound healing.

Attempts to overcome the problems associated with common wound dressings have been made by the use of various "body" dressings. Such body dressings are typically formed in the shapes of the body surfaces for which they are intended to cover and protect. Such body dressings which have been sold by Exu-Dry Wound Care Products, Inc., of the Bronx, New York, are specifically shaped to conform to the shapes of the head, arms/hand and leg/foot. Additionally, Exu-Dry also distributes torso dressings which are intended to cover the chest, abdomen and buttocks. All these body dressings have been made of non-occlusive materials. However, the torso dressings which have been sold by Exu-Dry are formed of front and rear panels which are permanently attached above the shoulder. The rear lateral sides of the panel wrap around the sides of the patient and are secured to each other both by means of hook and loop tape fasteners as well as string ties. While this construction has proven adequate for covering and conveniently examining the lower portions of the torso, they have not been practical in so far as the upper torso and the axilla or underarm areas are concerned. To examine and treat those areas, it has been necessary to separate the rear panel extensions from the front panel and lift the front panel almost totally over the head of the patient. Even under those conditions, access to the axilla and upper torso, including the shoulders, has been impractical and uncomfortable to the patient.

SUMMARY OF THE INVENTION

It is accordingly an object of the present invention to provide a dressing for the axilla and upper torso of the patient which does not exhibit the disadvantages inherent in prior art dressings.

It is another object of the present invention a dressing as in the previous object which is simple in construction and economical to manufacture.

It is still another object of the present invention to provide a dressing as in the aforementioned object, which minimizes discomfort and pain to the patient when the dressing is applied or removed and is conveniently manipulated by medical personnel.

It is yet another object of the present invention to provide a dressing of the type under discussion which is formed of highly conformable, non adherent, anti-shear material which is highly absorbent.

It is a further object of the present invention to provide a dressing of the type aforementioned which includes color coding means for facilitating application of dressing to the patient and for minimizing errors in doing the same.

It is yet a further object of the present invention to provide a dressing which is particularly adapted or suitable for treating the axilla and upper torso of the patient, by allowing the dressing to be opened from the region above the shoulder so that the front and rear panels making up the dressing can be lowered to expose the shoulder(s), axilla and upper torso portion of the body.

In order to achieve the above objects, as well as others which will become apparent hereinafter, a dressing in accordance with the present invention for covering the axilla and upper torso areas of a patient comprises a sheet of conformable material. Said sheet of conformable material includes a rear back portion which covers at least a part of the patient's back, said rear back portion forming a first sleeve portion, and at least one front chest portion which covers at least a part of the patient's chest, said front chest portion forming a second sleeve portion. Said first and second sleeve portions together form a generally fitted body dressings which includes at least a partial length sleeve to receive an arm of the patient. Connecting means is provided for releasably securing said first and second sleeve portions to each other and for selectively opening said sleeve portions to expose the shoulder, axilla and upper torso of the patient, whereby the dressing can be quickly and safely placed on and removed from the upper torso areas of the patient with minimum inconvenience and trauma to the injury sustained by the patient.

BRIEF DESCRIPTION OF THE DRAWINGS

Other objects and features of the present invention may become clear from the following description taken in conjunction with the preferred embodiment thereof, making reference to the accompanying drawings, in which:

FIG. 3 is a front elevational view of the front panel of the dressing shown in FIG. 2;

FIG. 4 is a front elevational view of the rear panel of the dressing shown in FIG. 2;

DESCRIPTION OF THE PREFERRED EMBODIMENTS

Figure 1:
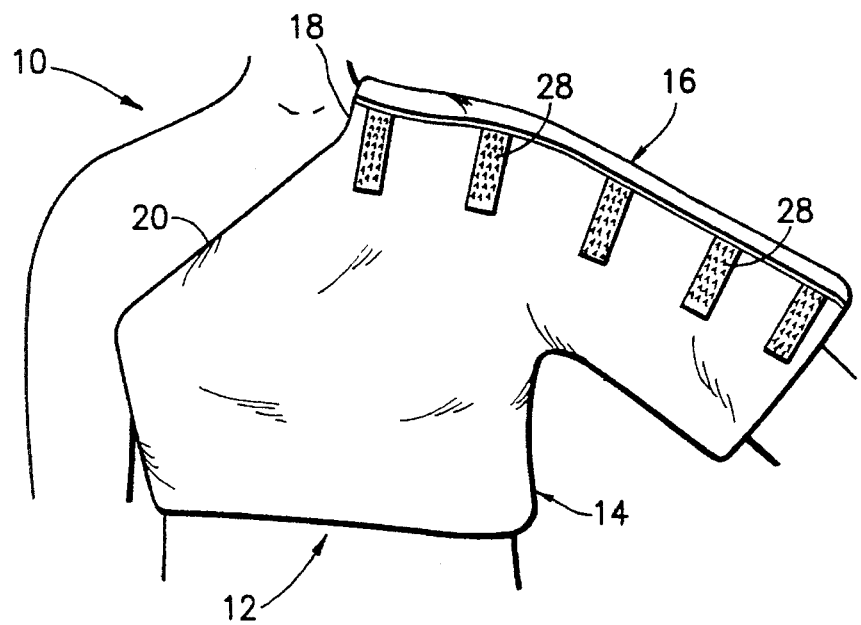
FIG. 1 is a perspective view of a dressing in accordance with one preferred embodiment of the present invention which includes one sleeve, shown positioned on a patient.

Referring now specifically to the drawings, in which the identical or similar parts are designated by the same reference numerals throughout, and first referring to FIG. 1, a dressing for covering the axilla and upper torso areas of a patient 10 is generally designated by the reference numeral 12.

As will be clear from FIG. 1, the dressing 12 represents an embodiment for partially covering the upper torso of the patient 10 since it covers only one shoulder while leaving the other shoulder exposed. An alternate embodiment which is illustrated in FIGS. 5–8 covers the entire upper torso including both shoulders.

The first embodiment 12 is essentially formed of a front panel 14 and a rear or back panel 16. The dressing 12 preferably has certain features and functional characteristics which are desirable in wound dressings for treating, for example, burns and major surgery. However, numerous materials may be used in order to practice the present invention and the invention is not limited to any one given material. In accordance with the presently preferred embodiments, the front and rear panels 14, 16 are formed of a sheet of conformable material, conformability or pliability being an important feature or characteristic of the material so that it may conform to the shape of the body in the regions proximate to the wound or wounds with minimum irritation or friction on the sensitive wound layers or tissues. One example of a conformable sheet material which can beneficially be used to practice the invention is a non-occlusive burn and trauma dressing disclosed in U.S. Pat. No. 4,667,665 issued on May 26, 1987 and assigned to the inventor of the present invention. The disclosure, teachings and suggestions in said aforementioned patent is incorporated by reference as if fully set forth herein. Briefly, such dressing material includes an absorbent layer covered a non-adherent outer wound contact layer and an intermediate anti-shear layer. The wound contact and anti-shear layers are preferably formed of two superimposed strata of perforated polyethylene film each having a thickness of approximately 4.3 mils, a density of 15 lbs per cubic feet and perforation spacing of 9 dots per centimeter. A suitable perforated polyethylene film for fabrication of the dressing is commercially available under the Trademark DELNET, manufactured by Applied Extrusion, P.O. Box 582, Middletown Del. 19709. The layers of this material are non adherent, permeable and non occlusive, as well as compatible with topical agents. Thus, while the body dressing 12 may consist of two or more panels, each of the panels is formed of a one piece multi layer design, which eliminates the need for multiple layers of dressing materials.

An important feature of such dressings is to allow the dressing to be adjusted to provide the proper amount of contact with the wound without applying excessive pressures which may cause discomfort or pain to the patient. In order to achieve this, the embodiment of the dressing 12 is provided with suitable connecting means for releasably securing the panels to each other and for allowing a degree of adjustability to, in essence, modify the effective size of the dressing. This allows the dressing to accommodate patients of slightly sizes and builds as well as apply the desired contact pressure against the wound.

Figure 2:
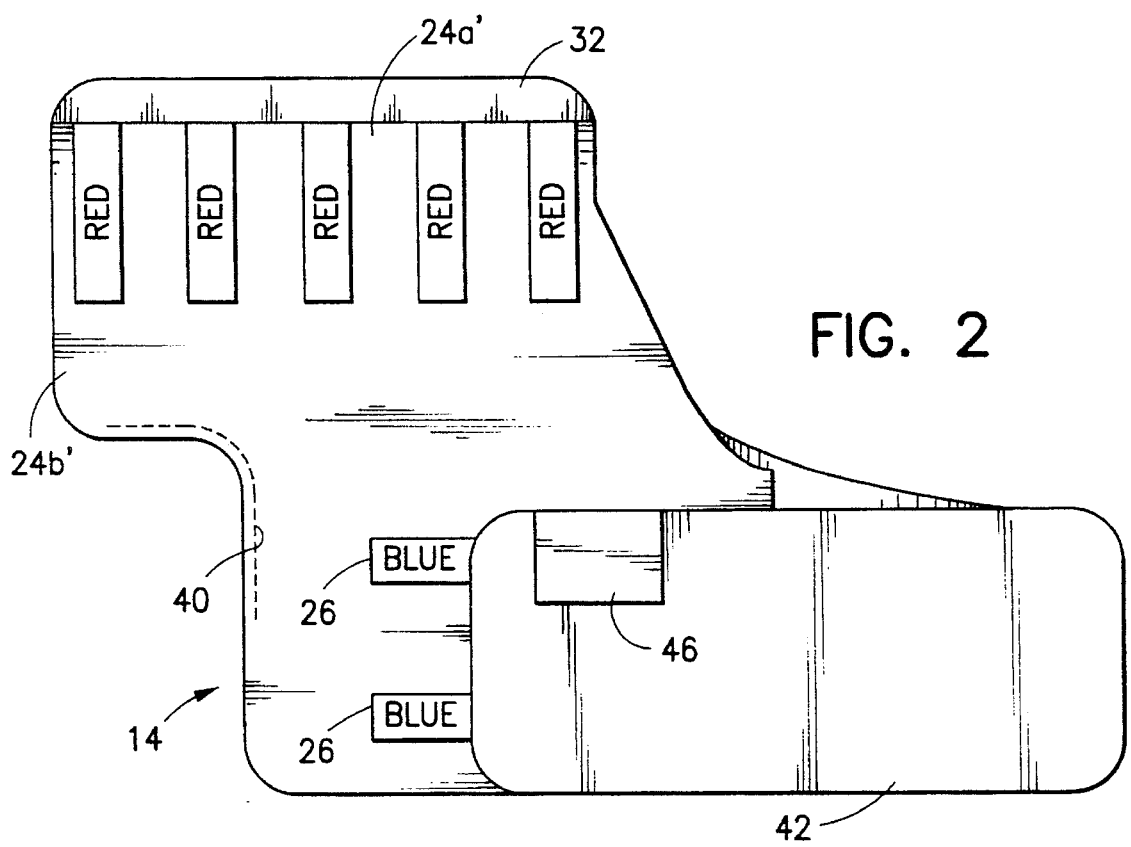
FIG. 2 is a front elevational view of the dressing shown in FIG. 1.

The embodiment illustrated in FIG. 1 is formed of two separate panels which are shown in their assembled state in FIG. 2 and in their disassembled state in FIGS. 3 and 4. Referring, thus, to FIGS. 1–4, the front panel or portion 14 is provided with a neckline 18 which becomes a diagonal chest line 20 which extends from the region of the neck of the patient to the axilla or underarm region on the opposite side of the body or below the opposing shoulder. A lower portion 22, which covers the chest area of the torso is provided with an upper portion 24 which is primarily configured to cover one of the shoulders of the patient as well as to form a sleeve portion 24b which extends laterally, towards the left as viewed in FIG. 3. A pair of connecting "hook" tapes 26 are illustrated on the lower portion 22 extending generally horizontally as viewed in FIG. 3, while a series of connecting "hook" tapes 28 are substantially equally spaced from the neckline 18 to an edge 30 of the sleeve portion 24b.

The rear panel or portion 16, best illustrated in FIG. 4, likewise includes a neckline 18' which likewise continues as a diagonal line 20' which extends along the back of the dressing to the axilla below the opposing shoulder, as with the front panel 14. As with the front panel, the rear panel 16 includes a lower torso covering portion 22' and an upper shoulder covering portion 24a' which includes a sleeve portion 24b'. The edge of the sleeve portion is indicated by the reference numeral 30'. Extending from the shoulder covering and sleeve portion 24' is a shoulder overlapping portion 32 which is intended to fold about folding line 34 to cover the top of the shoulder and bridge over to the front panel 14, as best shown in FIGS. 1 and 2. A horizontal section of connecting "loop" tape 36 is shown, the length of which is selected to bridge at least two or more of the strips of connecting "hook" tape 28 on the front panel 14, the tape 28, 36 forming connecting means for releasably securing the first and second sleeve portions 24, 24'. In this manner, the shoulder overlapping portion 32 can be releasably secured to the front panel or section 14 in the region of the shoulder for selectively opening the sleeve formed by the upper portions 24, 24' to expose the shoulder, axilla and upper torso of the patient when the connecting tape strips secure the front and rear panels. The lower edge 38, the upper portions 24, 24' and the adjoining edges 38' of the lower torso covering portions 22, 22' are advantageously stitched as indicated by the stitching 40 in FIG. 2. In this way, the dressing below the axilla and the lower portions 22, 22' of the dressing covering the lower torso are permanently attached to each other while the upper portions of the dressing may be easily and quickly opened or separated.

It will be evident, as clearly seen from FIGS. 1–4, that the amount of overlap by the shoulder overlapping portion 32 with the front panel 14 will be a function of the relative positions at which the connecting tapes 36 and 28 engage one another. By arranging these respective connecting tapes in relative orthogonal directions, as shown, the connecting tape 36 can be moved along the lengths of the connecting tapes 28 to provide suitable adjustments and to take out any slack or relieve any pressure on the shoulder area and control the contact pressure of the attached region of the dressing along the stitching 40 against the axilla or underarm area.

In order to adjust the dressing 12 for the size and build of the patient, as well as maintain or secure the dressing in place, the rear panel or section 16 is advantageously provided with a laterally extending back piece encircling portion 42 which serves as a form of an adjustable belt. The encircling portion 42 is provided with a series of generally transverse connecting "loop" tapes 44 which are preferably uniformly spaced from each other as shown. Referring to FIGS. 2 and 3, the front panel or section 14 is, in turn, provided with a pair of horizontal connecting "hook" tapes which are spaced from each other at a distance to generally correspond to the lengths of the connecting tapes 44 so that there may be engagement between these respective tapes upon contact when the encircling portion 42 is wrapped about the torso or the waist of the patient and the associated connecting tapes are brought into contact with each other. The tapes 266, 44 form connecting means for connecting the front chest and rear back portions 14, 16 to each other. It is clear that the encircling portion 42 together with the connecting tapes 26 and 44 allow for adjustment to compensate for the size and shape of the patient, as well as prevent the relative movements of the dressing along the shoulder and arm of the patient.

The dressing 12 is a partial dressing in that one shoulder is left uncovered. This dressing can readily be reversed so that the shoulder shown covered in FIG. 1 becomes uncovered, and the shoulder which is shown uncovered in FIG. 1 becomes covered. In that event, what has been described as being a rear panel would clearly become a front panel and what has been termed a front panel would become a rear panel. For this reason, the designations "front" and "rear" panels, for purposes of the present invention, are not critical and are merely used to facilitate a description of the invention. These terms can be interchanged, depending on the manner in which the dressings are used.

Although not critical, the dressing 12 is preferably provided with color coded connecting means to facilitate, expedite and prevent errors in the application of the dressings to the patient. In the embodiment illustrated, such connecting means is in forms of connecting "hook" and "loop" tapes which are commonly sold under the Trademark "VELCRO". In order to assure that the connecting tape 36 is always connected to the connecting tapes 28 they are both color coded with the same color and, in the example shown, both are red. Similarly, the tapes 44 on the encircling portion 42 as well as the tapes 26 on the front panel 14 are both blue in color. Although these connecting elements are in the form of connecting tape it should be clear that any means for detachably connecting these panels to each other and providing the requisite adjustability can be used. Thus, for example, ties can also be used and these can, likewise, be color coded.

Referring to FIG. 2, the dressing is advantageously provided with an optional label 46 2which advises the user to apply the reverse side of the panel against the wound.

Referring to FIGS. 5–8, a second embodiment 48 of the dressing is illustrated which is a full dressing since it simultaneously covers both shoulders. The construction and use of the vest is essentially the same, with the following exceptions. The dressing 48 is formed of three separate panels including a right front chest portion or panel 50 shown in FIG. 6, a left chest portion or front panel 52 shown in FIG. 7 and a back portion or rear panel 54 illustrated in FIG. 8. The front panels 50, 52 are stitched to the rear panel 54 along the same edges 38, 38' as with the first embodiment 12 with stitching 40 shown in FIG. 5. However, the rear panel 54 is now provided with a modified lower portion 22" and two upper torso and sleeve portions 24a', 24b', 24a" and 24b", respectively, each having associated therewith a shoulder overlapping portion 32, 32' each of which can be folded at associated folding lines 34.

Figure 6:
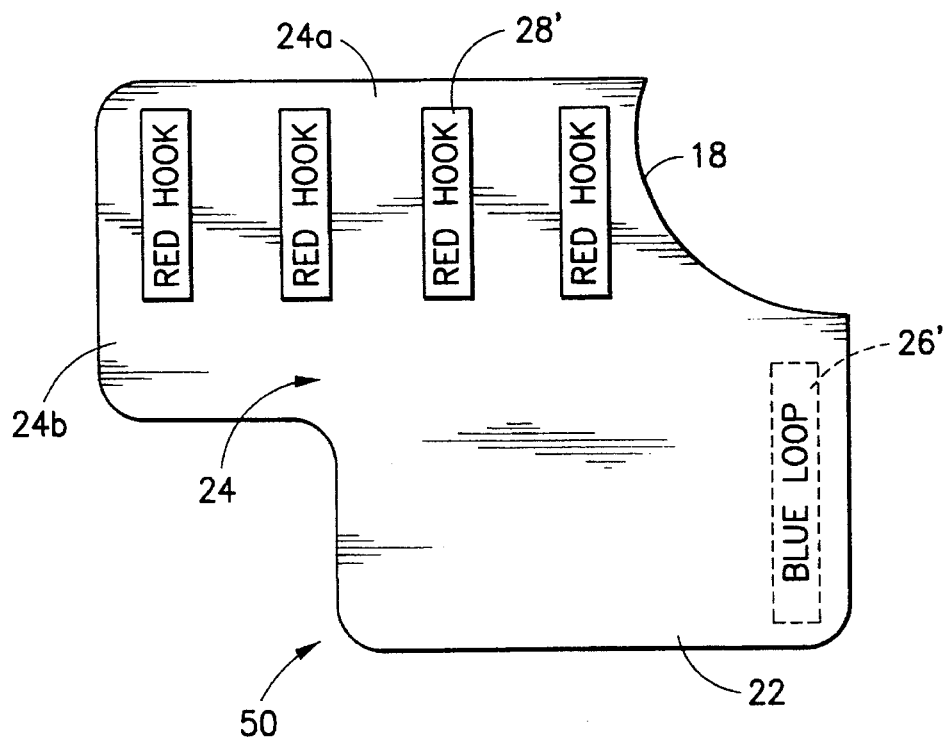
FIG. 6 is a front elevational view of the right front or panel of the dressing shown in FIG. 5.
Figure 7:
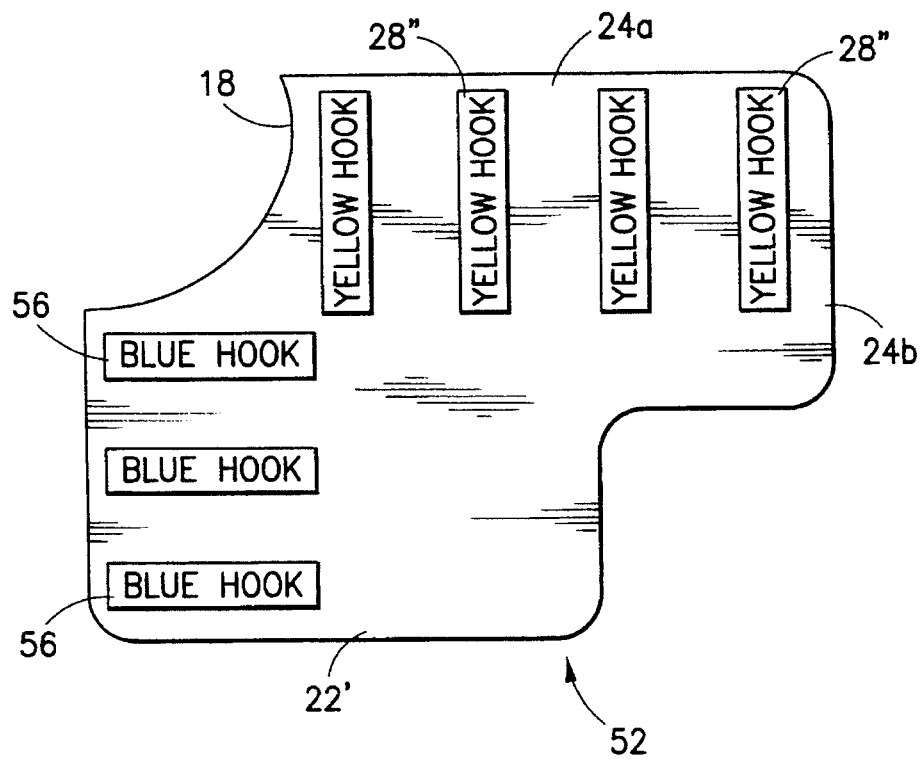
FIG. 7 is similar to FIG. 6 but showing the left front panel of the dressing shown in FIG. 5
Figure 5:
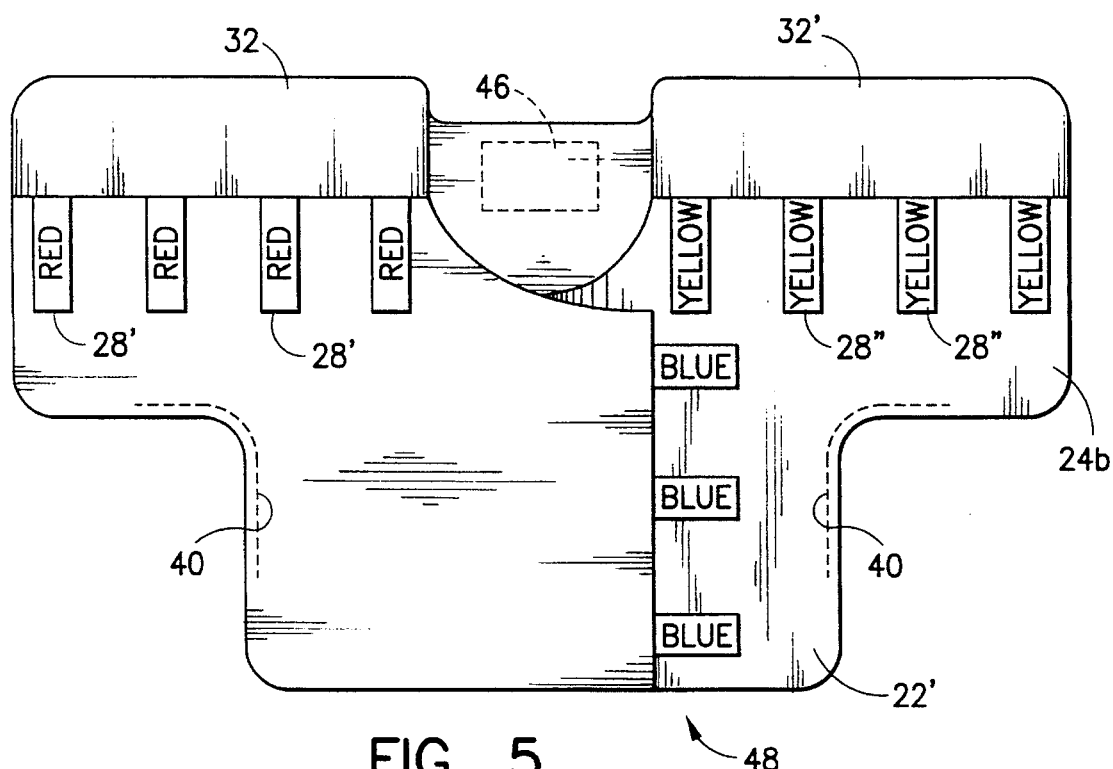
FIG. 5 is a front elevational view of another embodiment in accordance with the present invention which includes two sleeves, as opposed to the single sleeve version shown in FIGS. 1 and 4.
Figure 8:
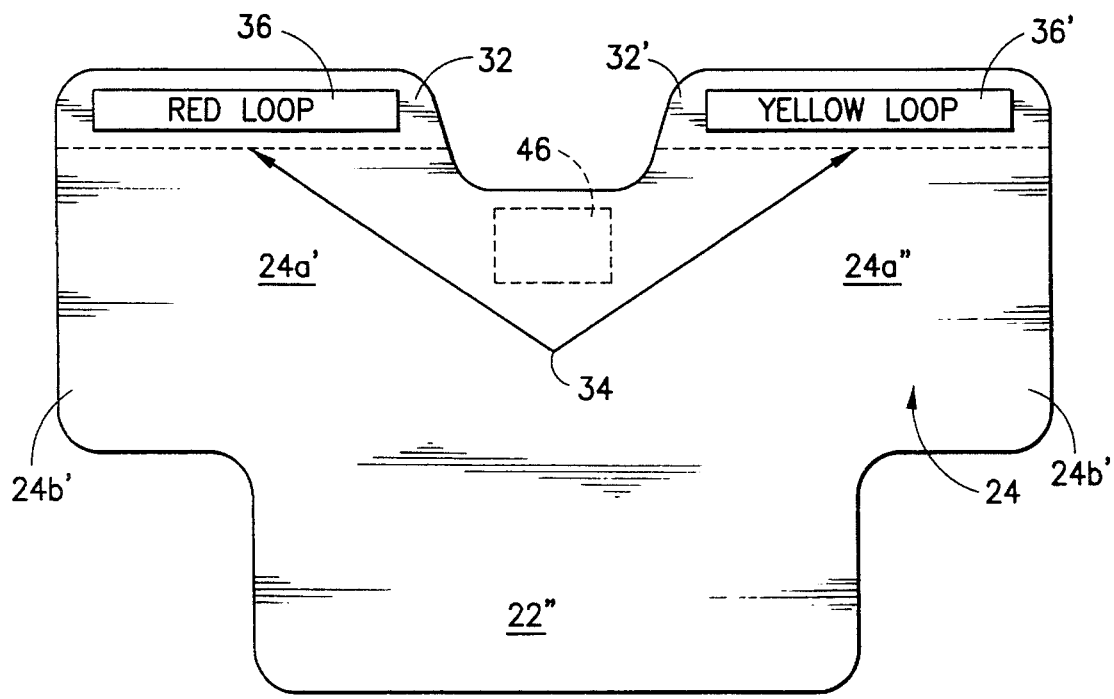
FIG. 8 is a front elevational view of the rear or back piece or panel of the dressing shown in FIG. 5.

The shoulder overlapping portion 32 is provided with a connection "loop" tape 36 as shown in FIG. 8. The opposing shoulder overlapping portion 32' is provided with a corresponding connection "loop" tape 36' which is similarly oriented and generally of the same length as the tape 36. Referring to FIG. 6, the right front panel 50 is provided with a series of four connecting "hook" tapes 28' similar to the tapes 28 shown in FIG. 3. However, the two connection "hook" tapes 26 in FIG. 3 have been replaced by a single connecting "loop" tape 26' which is arranged in the same general orientation as the aforementioned connecting tapes 28' on the panel 50. In FIG. 7, the opposing or left front panel 52 is also provided with a series of connecting "hook" tapes 28" similar to the tapes 28, 28' shown in FIGS. 3 and 6. The lower torso portion 22' of the panel 52 is provided with a series of generally horizontal equally spaced "hook" tapes 56 which are arranged to engage the loop connecting tape 26' on the right front panel 50, as shown in FIG. 6, while the connecting "loop" tapes 36, 36' the rear panel 54 shown in FIG. 8 are arranged to engage the upper connecting tapes 28', 28" of the respective right and left front panels 50, 52 shown in FIGS. 6 and 7. It will be evident that the specific orientations of the various connecting loop and hook tapes is not critical for purposes of the present invention and any orientations which will provide suitable connections may be used. Thus, the orientations of the associated "hook" and "loop" tapes can easily be reversed so that the ones that are shown to be horizontal can be made vertical and vice versa.

As with the first described embodiment, a label 46 is also advantageously stitched onto the back of the rear panel 54 containing instructions to ensure that the user is advised as to which side of the panel is to be applied to the wound.

Adjustability in the shoulder area is precisely as described in connection with the first mentioned embodiment 12, adjustability of the shoulder overlapping portions 32 in relation to the front panel or panels effectively decreasing the size of the shoulder and arm receiving portions thereby effectively lifting or dropping the dressing in relation to the level of the shoulders. This, in turn, determines the clearances between the surfaces of the wounds and the contact pressures of the wound tissues against the inner surfaces of the dressing. In the second embodiment 48, however, in place of the lateral adjustability use of the encircling positions of the encircling portion 42 such lateral adjustability is provided by the relative positions and/or relative overlapping of the right and left front panels 50, 52.

While certain ones of the connecting tapes have been described as "hook" tapes and the mating tapes have been described as being "loop" tapes, it is clear that these can be reversed so that the hook tapes can be made to be loop tapes and vice versa.

Although the present invention has fully been described in connection with the preferred embodiments thereof with reference to the accompanying drawings, it is to be noted that various changes and modifications are apparent to those skilled in the art. Such changes and modifications are to be understood as included within the scope of the present invention as defined in the claims that follow.

I claim:

1. A dressing for coveting the axilla and upper torso areas of a patient comprising a sheet of conformable material, said sheet of conformable material including a rear back portion which covers at least a part of the patient's back, said rear back portion forming a first sleeve portion, and at least one front chest portion which covers at least a part of the patient's chest, said front chest portion forming a second sleeve portion, first connecting means for connecting said front chest portion and rear back portion to secure the dressing about the torso of the patient, said first and second sleeve portions together forming a generally fitted dressing at least for the upper arm which includes at least a partial length tubular sleeve to only receive and fully surround at least a portion of an arm of the patient; and second connecting means along said tubular sleeve for releasably securing said first and second sleeve portions and for selectively opening said sleeve to expose the shoulder, axilla and upper torso of the patient when said connecting means secures said first and second sleeve portions, whereby the dressing can be quickly and safely placed on and removed from the patient with minimum inconvenience and trauma to the injuries sustained by the patient and the patient with minimum inconvenience and away from the region of the torso.

2. A dressing as defined in claim 1, wherein said sheet of conformable material includes at least a portion formed of bandaging material.

3. A dressing as defined in claim 1, wherein said rear back and front chest portions are formed of a single piece conformable material.

4. A dressing as defined in claim 1, wherein said sheet of material includes a non-adherent surface layer.

5. A dressing as defined in claim 4, wherein said non-adherent surface layer comprises an anti-shear layer.

6. A dressing as defined in claim 1, wherein said sheet of material includes a highly absorbent material.

7. A dressing as defined in claim 1, wherein said fitted dressing has one sleeve and a neck line which extends from said one sleeve on one side of the body to the area of the axilla to the other side of the patient's body by means of a generally diagonal torso line.

8. A dressing as defined in claim 1, wherein said rear back portion covers the entire back of the patient and forms two first sleeve portions; and two front chest portions each of which covers at least a part of patient's chest and forms a second sleeve portion, said first and second sleeve portion's together forming a generally fitted dressing which includes at least two partial length sleeves to receive both arms of the patient, separate connecting means being provided for each of said two partial length sleeves.

9. A dressing as defined in claim 1, wherein said connecting means comprising cooperating hook and loop fastener tapes secured to selected portion of said rear back and front chest portions.

10. A dressing as defined in claim 1, wherein said fastener tapes are color coded to assure proper attachment of said front and rear portions.

11. A dressing as defined in claim 1, further comprising an instruction label on one surface of said material to advise that the opposite surface is to be applied to the wound or skin of the patient.

12. A dressing as defined in claim 1, wherein said connecting means comprises strips of connecting hook and loop fastener tape.

13. A dressing as defined in claim 12, wherein cooperating strips of tape are color coded to assure proper connection and prevent improper application of the dressing on the patient.

14. A dressing as defined in claim 1, wherein said connecting means comprises a plurality of cooperating ties.

15. A dressing as defined in claim 14, wherein cooperating ties are color coded to assure proper connection and prevent improper application of the dressing on the patient.

16. A dressing as defined in claim 1, wherein said front and rear portions are permanently attached to each other in the region of the dressing that covers the axilla.

17. A dressing as defined in claim 16, wherein said front and rear portions are stitched together in the region of the axilla.

18. A dressing as defined in claim 12, wherein cooperating strips of connecting tape are arranged substantially orthogonally to each other.

\* \* \* \* \*